United States Patent [19]
Ueno et al.

[11] Patent Number: 5,770,766
[45] Date of Patent: Jun. 23, 1998

[54] METHOD FOR SEPARATING AND PURIFYING HYDROXYNAPHTALENECARBOXYLIC ACIDS

[75] Inventors: Ryuzo Ueno, Nishinomiya; Masaya Kitayama, Takarazuka; Kuniyo Yanagawase, Ibaraki; Yoshiro Uchiyama, Nishinomiya; Shigeji Mori, Itami, all of Japan

[73] Assignee: Kabushiki Kaisha Ueno Seiyaku Oyo Kenkyujo, Osaka, Japan

[21] Appl. No.: 860,803

[22] PCT Filed: Nov. 12, 1996

[86] PCT No.: PCT/JP96/03314

§ 371 Date: Jul. 10, 1997

§ 102(e) Date: Jul. 10, 1997

[87] PCT Pub. No.: WO97/18182

PCT Pub. Date: May 22, 1997

[30] Foreign Application Priority Data

Nov. 13, 1995 [JP] Japan .................... 7-294335

[51] Int. Cl.$^6$ ..................... C07C 63/34
[52] U.S. Cl. ..................... 562/467
[58] Field of Search ............. 562/467

[56] References Cited

FOREIGN PATENT DOCUMENTS

| 341594 | 11/1989 | European Pat. Off. |
| 3800989 | 7/1989 | Germany |
| 149149 | 5/1992 | Japan |
| 306007 | 11/1994 | Japan |

*Primary Examiner*—Paul J. Killos
*Attorney, Agent, or Firm*—Sughrue, Mion, Zinn, Macpeak & Seas, PLLC

[57] ABSTRACT

The present invention provides a method for effectively separating independent hydroxynaphthalene-carboxylic acids by treating a mixture containing various kinds of hydroxynaphthalene-carboxylic acids with nonionic porous synthetic adsorbents having as a basic structure aromatic copolymers mainly composed of styrene and divinyl benzene or methacryl copolymers mainly composed of monomethacrylates and dimethacrylates.

3 Claims, 7 Drawing Sheets

METHOD FOR SEPARATING AND PURIFYING HYDROXYNAPHTALENECARBOXYLIC ACIDS

TECHNICAL FIELD AND BACKGROUND

The present invention relates to a method of separation and purification of hydroxynaphthalenecarboxylic acids.

Hydroxynaphthalenecarboxylic acids such as 2-hydroxynaphthalene-6-carboxylic acid are important raw materials of aromatic polyesters, and indispensable especially to the production of liquid crystalline polymers excellent in workability and fluidity, and resins or fibers having a high elasticity and a high heat resistance. Further, 2-hydroxynaphthalene-3-carboxylic acid and 2-hydroxynaphthalene-3,6-dicarboxylic acid are useful as raw materials for azo type pigments or dyes.

2-hydroxynaphthalene-6-carboxylic acid (referred to as "BON6" hereinafter) and 2-hydroxynaphthalene-3-carboxylic acid (referred to as "BON3" hereinafter) have been produced from the reaction of alkaline salts of β-naphthol and carbon dioxide by Kolbe-Schmitt reaction (Japanese Patent Application KOKAI Sho. 57-95939, Japanese Patent Application KOKAI Sho. 57-97244, Japanese Patent Application KOKAI Sho. 58-99436, and Japanese Patent Application KOKAI Sho. 63-146843 etc.). The reaction mixtures obtained according to the above reaction contain isomers such as BON3, BON6 and other impurities in addition to objective products.

Recently, it has been found that 2-hydroxynaphthalene-3,6-dicarboxylic acid (referred to as "BON3,6" hereinafter) can be obtained in high yield by the reaction of potassium salt of 2-naphthol and carbon dioxide under a specific condition, but substantial amounts of BON6 and BON3 are still contained in the reaction mixture.

As these hydroxynaphthalenecarboxylic acids vary in the use and property, the purification of the products is indispensable, and various purification processes therefor have been proposed.

For example, as a method for the separation and purification of BON6, the process has been proposed in which water is added to the reaction mixture and the pH value is adjusted at approximately 3–4 with a mineral acid such as hydrochloric acid, sulfuric acid and the like to deposit a crude BON6, and then the crude product is washed with water-alcohol solvent such as diluted methanol to separate BON6 and BON3.

Other method such that crude BON6 are subjected to crystallization in an aqueous solution containing aliphatic ethers (Japanese Patent Application KOKAI Hei 1-216955), and the BON6 is separated by the crystallization as the dioxane adduct so as to obtain the BON6 from the adduct (Japanese Patent Application KOKAI Hei 2-15046 and KOKAI Hei 2-218643).

Similar methods have been used for the separation of BON3,6 from BON3 and BON6, but these methods were not sufficient and it was impossible to obtain separated and purified products in a high purity from the reaction mixtures containing impurities in much amount.

DISCLOSURE OF THE INVENTION

The present invention relates to a method of separation and purification of hydroxynaphthalenecarboxylic acids, which comprises treating a solution containing a mixture of various kinds of hydroxynaphthalenecarboxylic acids with a nonionic porous synthetic adsorbent having as a basic structure aromatic copolymers mainly composed of styrene and divinylbenzene or methacrylic copolymers mainly composed of monomethacrylates and dimethacrylates, and separating into each hydroxynaphthalenecarboxylic acid.

In the present specification, "treatment with adsorbents" means a process including a previous dissolution of hydroxynaphthalenecarboxylic acids in a solvent, an adsorption of the solution obtained, and a selective extraction with a solvent or an elution through a column packed with an adsorbent.

In the present specification, "hydroxynaphthalenecarboxylic acids" include not only hydroxynaphthalene monocarboxylic acids but also polycarboxylic acids such as dicarboxylic acids, tricarboxylic acids, tetracarboxylic acids and the like.

The nonionic porous synthetic adsorbents having as the basic structure aromatic copolymers mainly composed of styrene and divinylbenzene or methacrylic copolymers mainly composed of monomethacrylates and dimethacrylates usable in the present invention are known. As the nonionic porous synthetic adsorbents having as a basic structure aromatic copolymers mainly composed of styrene and divinylbenzene include DIAION (trade name; available from Mitsubishi Kagaku K. K.) HP10, HP20, HP21, HP30, HP40, HP50, SP850 and SP205, AMBERLITE (trade name; available from Rohm & Haas Co.) XAD2 and XAD4, and the like, and as the nonionic porous synthetic adsorbents having as a basic structure methacrylic copolymers mainly composed of monomethacrylates and dimethacrylates as main monomers include DIAION HP2MG, AMBERLITE XAD7 and XAD8, and the like.

The nonionic porous synthetic adsorbents usable in the present invention are porous crosslinked polymers, and have a specific surface area and a pore volume in significant quantities. The adsorbents have suitably a specific surface area of not less than 100 $m^2/g$, preferably not less than 400 $m^2/g$, and a pore volume of not less than 0.1 ml/g, preferably 1.0 ml/g or more. In case of the adsorbents having a specific surface area of less than 100 $m^2/g$ or a pore volume of less than 0.1 ml/g the adsorbing amount is influenced and the separating ability tends to become worse.

As aforementioned, BON6 is prepared according to Kolbe-Schmitt reaction, in which BON3 is produced as a by-product. The amount of BON3 as by-product depends on the process of production of BONG, but the BON3 itself is a useful compound as a raw material of pigments or dyes. Accordingly one of the purpose of the present invention is to separate BON6 and BON3, by which can be also achieved the purification of BON6 containing other impurities or by-products.

According to the present invention, BON3 is more strongly adsorbed by the above adsorbents than BON6, and other impurities are also adsorbed. Therefore, when the solution containing BON6 with the impurities and the by-products such as BON3 is treated with the above adsorbents, these impurities and by-products are adsorbed so as to eliminate them from the solution containing BON6.

A mixture of hydroxynaphthalenecarboxylic acids containing BON3 as main products can be also prepared according to Kolbe-Schmitt reaction. In this case, since BON6 is produced as a by-product, BON6 is firstly eluted, and BON3 is secondly eluted with the same or other solvent. Depended on the reaction condition BON3,6 is also produced as a by-product. In this case, BON6 is firstly eluted, and then it may be recovered with the same or other solvent as set forth hereinafter.

Further, BON3,6 is useful as a raw material for azo type pigments or dyes, and as aforementioned, a reaction mixture for production of BON3,6 contains BON3 and BON6. It has been found that BON3,6 has an almost intermediate adsorptivity to the nonionic porous synthetic adsorbent between that of BON3 and BON6. Accordingly it can be also separated or purified by a similar manner. For example, when the mixture of BON3, BON6 and BON3,6 is eluted through a column with the nonionic porous synthetic adsorbent, BON6, BON3,6 and BON3 are recovered in this order. In case of the mixture of BON6 and BON3,6, the BON6 is firstly eluted, and in case of the mixture of BON3 and BON3,6, the BON3,6 is firstly eluted.

According to the present invention, the separation and recovery of hydroxynaphthalenecarboxylic acids adsorbed may be achieved by a solvent which can dissolve objective hydroxynaphthalenecarboxylic acids. As such solvents there are exemplified polar solvents, for example, alcohols such as methanol, n-propanol and the like; ketones such as acetone, methyl ethyl ketone and the like; ethers such as diethyl ether, tetrahydrofuran and the like; amides such as dimethylformamide and the like; sulfur compounds such as dimethylsulfoxide and the like; aliphatic hydrocarbons such as hexane, heptane and the like; aromatic hydrocarbons such as benzene, toluene and the like; organic acids such as acetic acid and the like; organic acids esters such as ethyl acetate and the like; and water. These solvents may be selected according to the kinds of adsorbents. Preferable solvents are alcohols, especially methanol. Two or more kinds of solvents can be used as mixed if desired.

BON3, BON3,6 and BON6 may be separated and purified depended on the difference of adsorptivity to an adsorbent using a single solvent which can dissolve them, or recovered by selective extraction using a solvent which can specifically dissolve the objective compound, or successively eluted using solvents having a different solubility to each compound.

The treatment by the nonionic porous synthetic adsorbents may be carried out by a batch process or a continuous process, and any method of an adsorbing separation process by a batchwise operation or an elution using a column.

When the column is used for the treatment of the present invention, an adsorption column chromatography is convenient. As a developing solvent for the column chromatography, any solvent which can dissolve BON6, BON3, and BON3,6 may be used. As such solvents, there are concretely exemplified alcohols such as methanol, n-propanol and the like; ketones such as acetone, methyl ethyl ketone and the like; ethers such as diethyl ether, tetrahydrofuran and the like; amides such as dimethylformamide and the like; sulfur compounds such as dimethylsulfoxide and the like; aliphatic hydrocarbons such as hexane, heptane and the like; aromatic hydrocarbons such as benzene, toluene and the like; organic acids such as acetic acid and the like; organic acid esters such as ethyl acetate and the like; and water. These solvents can be selected according to the kinds of adsorbents. Preferable solvents are alcohols, especially methanol. Two or more kinds of solvents can be used as mixed if desired. The separation ability can be improved by controlling the ratio of the mixture. The development may be carried out by successive alternation of the solvents.

The present invention may be also used to increase the ratio of objective hydroxynaphthalenecarboxylic acids by repeating the treatment of the invention. Alternatively the concentration and ratio of the objective hydroxynaphthalenecarboxylic acids may be increased using an artificial moving bed and the like as described in Japanese Patent Application KOKAI Hei 2-49159.

According to the present invention, the hydroxynaphthalenecarboxylic acids can be purified to a sufficient level for industrial practical use, but when a higher purity is still required, known purification methods such as recrystallization may be used.

The present invention is illustrated using BON6, BON3, and BON3,6, but it is not restricted to these hydroxynaphthalenecarboxylic acids.

EXAMPLE

Example 1

As a column for separation and purification, a glass column (inner diameter of 28 mm and length of 400 mm) is packed with 200 ml of a nonionic porous synthetic adsorbent containing as a basic structure aromatic copolymers mainly composed of styrene and divinylbenzene (DIAION HP20, available from Mitsubishi Kagaku K. K., specific surface area: 605 m²/g pore volume (mercury porosimetry): 1.18 ml/g) as suspended in methanol. On the other hand, BON6 (available from Ueno Seiyaku K. K.) 2.9 g and BON3 (available from Ueno Seiyaku K. K.) 11.0 g were dissolved in methanol to prepare a solution 100 g.

The solution 5.0 g was weighed to put into the upper portion of the synthetic adsorbent layer in the column packed, and then developed as eluting methanol at a rate of 6.2 ml/minute at room temperature. The methanol solution eluted from the outlet of the column was fractionated about every 15 ml up to about 400 ml in total.

The each fraction was weighed, and then the concentrations of each of BON6 and BON 3 therein were determined by a high speed liquid chromatography (600 E type pump, 441 type UV detector, made by Waters Corp.).

Figure 1:
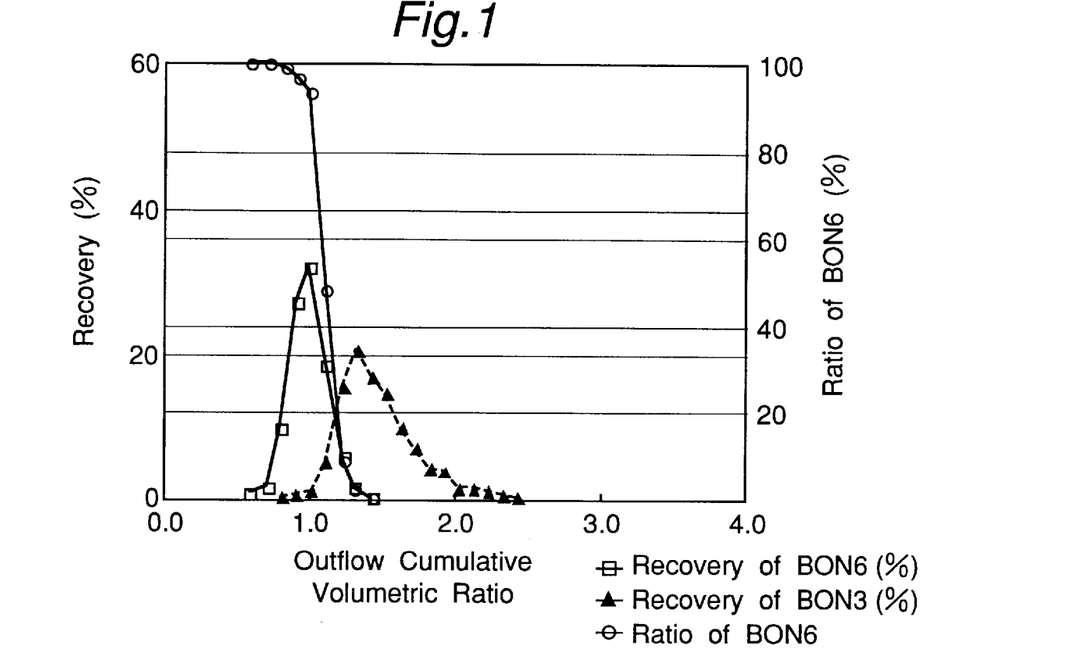
FIG. 1 is a graph illustrating the recovering ratios of each of BON6 and BON3 to the outflow cumulative volumetric ratio, and the change of ratio of BON6 in Example 1.

According to the result of analysis, the amount of the eluted methanol is converted to the volumetric ratio of the packed adsorbent (referred to as outflow cumulative volumetric ratio hereinafter) and recorded on the abscissa. According to the following equations, the recoveries of each of BON6 and BON3, and the ratio of BON6 in each fraction was calculated, which was showed in FIG. 1.

$$\text{Recovery of } BON6 \ (\%) = \frac{\text{weight of } BON6 \text{ in fraction}}{\text{weight of } BON6 \text{ in 5 g of solution}} \times 100$$

$$\text{Recovery of } BON3 \ (\%) = \frac{\text{weight of } BON3 \text{ in fraction}}{\text{weight of } BON3 \text{ in 5 g of solution}} \times 100$$

$$\text{Ratio of } BON6 \ (\%) = \frac{\text{weight of } BON6 \text{ in fraction}}{\text{weight of } BON6 \text{ and } BON3 \text{ in fraction}} \times 100$$

As apparent from FIG. 1, BON6 was eluted in the fractions of the outflow cumulative volumetric ratio of 0.6–1.4, and BON3 eluted in the each fraction of 0.8 to 2.4, and the both could be separated. Further, BON6 could be recovered in a ratio of not less than 93% and a recovery of 71.4% in the outflow cumulative volumetric ratio of 0.5–1.0. The ratio of BON3 was not less than 98% and the recovery was 78.5%.

Example 2

The methanol was developed according to the same manner as Example 1 except to use DIAION SP850 (specific surface area: 995 m²/g, pore volume (nitrogen porosimetry): 1.20 ml/g, available from Mitsubishi Kagaku K. K.) was used; the amount of BON6 in the solution was 2.8 g and the amount of BON3 was 11.4 g, and the methanol solution eluted from the outlet of the column was fractionated every about 30 ml.

According to the same manner as Example 1, each fraction was weighed, the concentrations of BON6 and BON3 in each fractionated solution were determined, and the recovery of each of BON6 and BON3 in each fraction, and the ratio of BON6 were calculated. The results were shown in FIG. 2.

Figure 2:
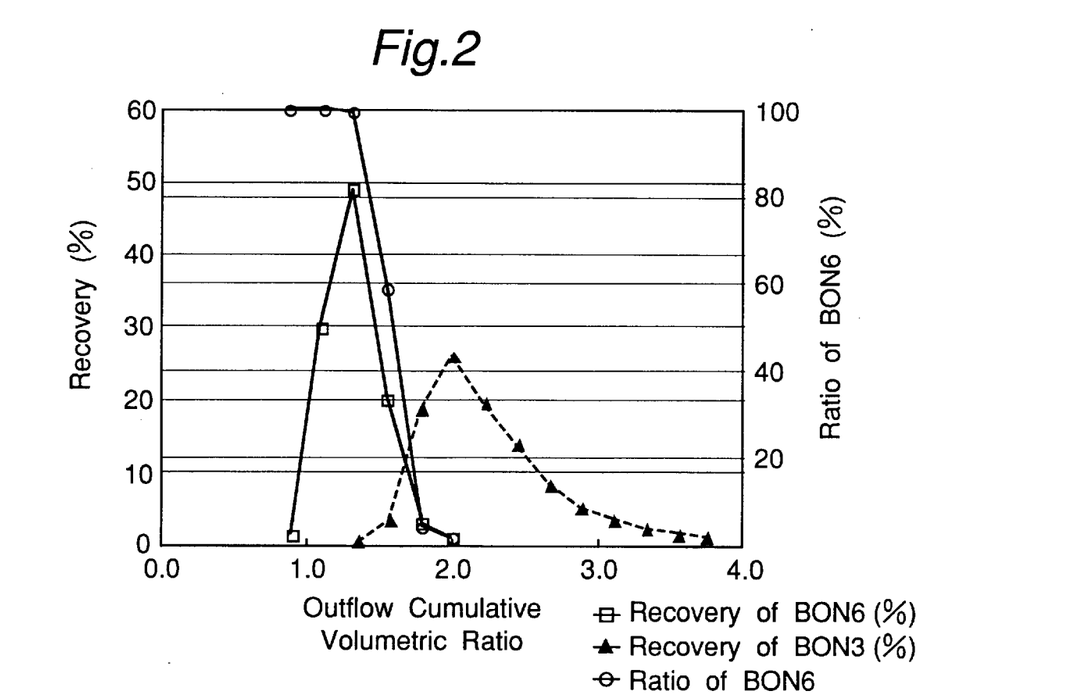
FIG. 2 is a graph illustrating the recovering ratios of each of BON6 and BON3 to the outflow cumulative volumetric ratio, and the change of ratio of BON6 in Example 2.

As apparent from FIG. 2, BON6 was eluted in the fractions of the outflow cumulative volumetric ratio of 0.8–2.0, and BON3 was eluted in the fractions of 1.3–3.8, so that the both could be separated. Further, BON6 could be recovered at the ratio of not less than 99% and the recovery of 79.2% in the outflow cumulative volumetric ratio of 0.9–1.1. The ratio and the recovery of BON3 were not less than 96% and 96.4% respectively.

Example 3

The methanol development was carried out according to the same manner as Example 2 except that DIAION SP205 (specific surface area: 507 m²/g, pore volume (mercury porosimetry): 1.04 ml/g, available from Mitsubishi Kagaku K. K.) was used as a adsorbent.

According to the same manner as the Example 2, each fraction was weighed, the concentrations of BON6 and BON3 in each fractionated solution were determined, and the recovery of each of BON6 and BON3 in each fraction and the ratio of BON6 were calculated. The results were shown in FIG. 3.

Figure 3:
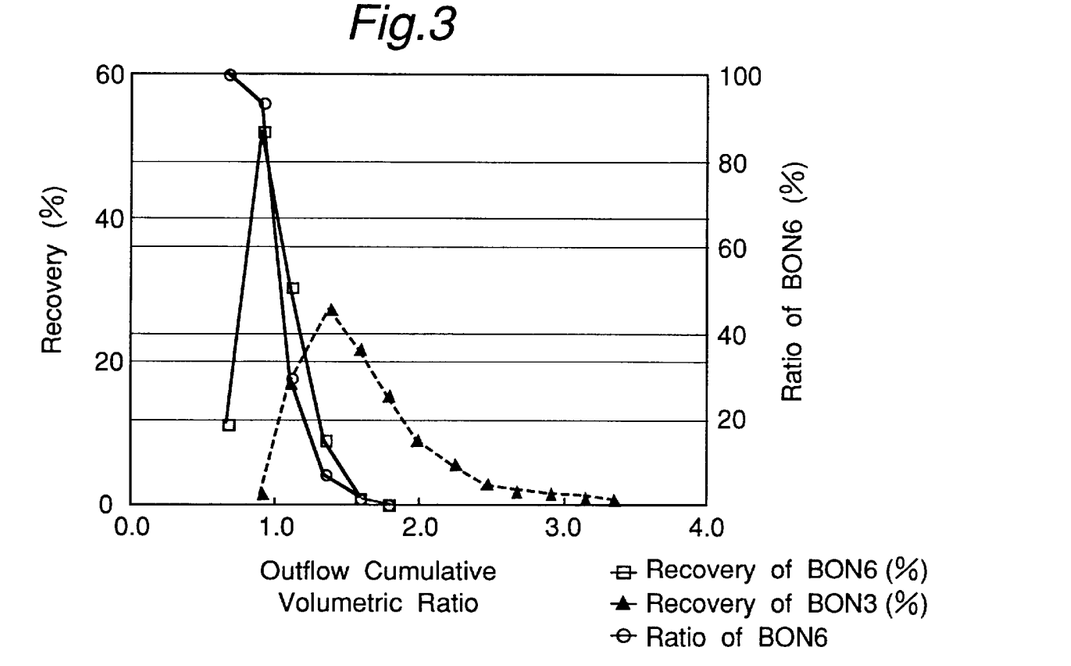
FIG. 3 is a graph illustrating the recovering ratios of each of BON6 and BON3 to the outflow cumulative volumetric ratio, and the change of ratio of BON6 in Example 3.

As apparent from FIG. 3, BON6 was eluted in the fractions of the outflow cumulative volumetric ratio of 0.6–1.8, and BON3 was eluted in the fractions of 0.9–3.4, so that the both could be separated. Further, BON6 could be recovered at a ratio of not less than 92% and a recovery of 63.0% in the outflow cumulative volumetric ratio of 0.7–0.9. The ratio and the recovery of BON3 were not less than 92% and 81.5% respectively.

Example 4

The methanol development was carried out according to the same manner as Example 2 except that DIAION HP2MG (nonionic porous synthetic adsorbent having as a main structure methacrylic type copolymers mainly composed of monomethacrylates and dimethacrylates; specific surface area: 473 m²/g, pore volume (mercury porosimetry): 1.15 ml/g, available from Mitsubishi Kagaku K. K.) was used as an adsorbent.

According to the same manner as Example 2, each fraction was weighed, the concentrations of BON6 and BON3 in each fractionated solution were determined, and the recovery of each of BON6 and BON3 in each fraction and the ratio of BON6 were calculated. The results were shown in FIG. 4.

Figure 4:
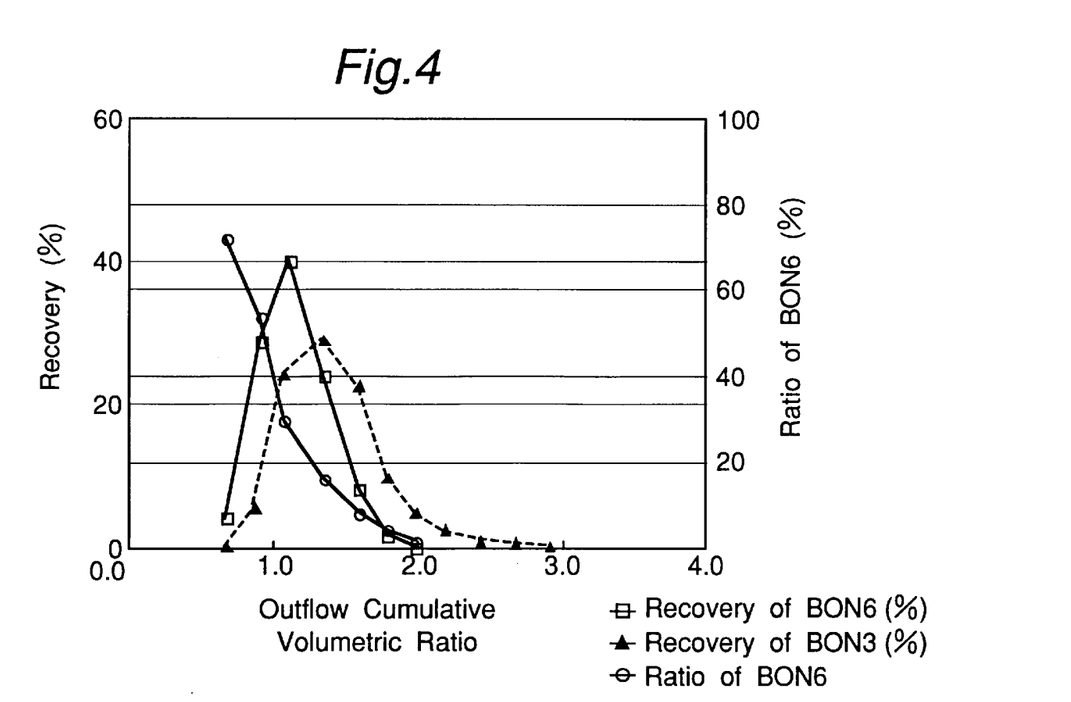
FIG. 4 is a graph illustrating the recovering ratios of each of BON6 and BON3 to the outflow cumulative volumetric ratio, and the change of ratio of BON6 in Example 4.

As apparent from FIG. 4, BON6 was eluted in the fractions of the outflow cumulative volumetric ratio of 0.6–2.0, and BON3 was eluted in the fractions of 0.9–2.9, so that the both can be separated. Further, BON6 could be recovered at the ratio of not less than 52% and a recovery of 32.8% in the outflow cumulative volumetric ratio of 0.7–0.9. The ratio and the recovery of BON3 were not less than 91% and 33.2% respectively.

Comparative Example 1

The methanol development was carried out according to the same manner to Example 2 except that a cationic ion exchange resin (DIAION PK216H, available from Mitsubishi Kagaku K. K.) was used as an adsorbent.

Figure 5:
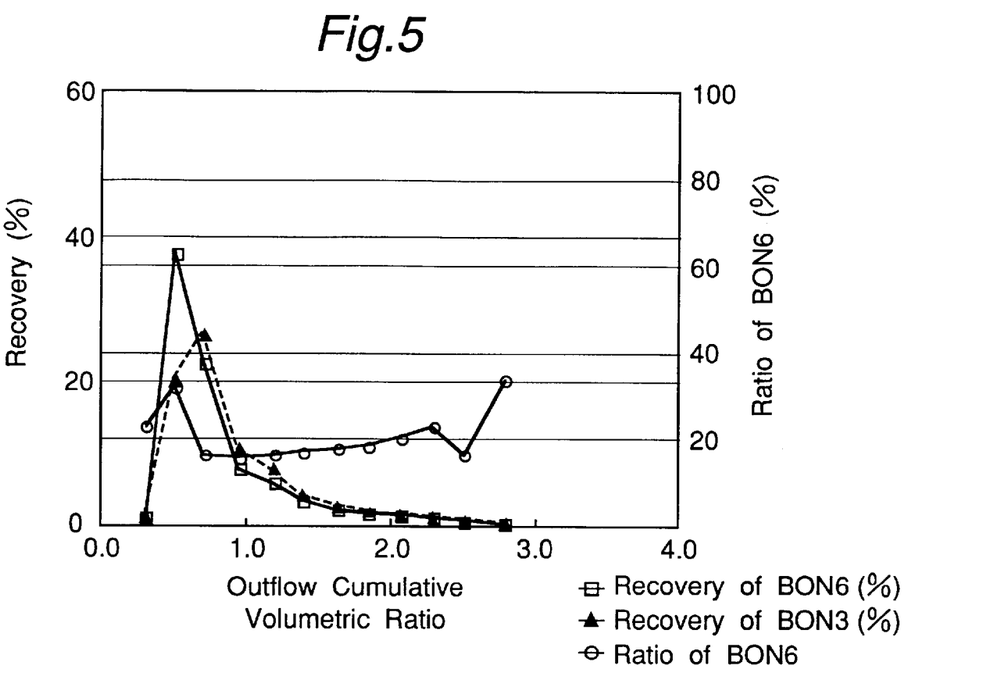
FIG. 5 is a graph illustrating the recovering ratios of each of BON6 and BON3 to the outflow cumulative volumetric ratio, and the change of ratio of BON6 in Comparative Example 1.

According to the same manner as Example 2 each fraction was weighed, the concentrations of BON6 and BON3 in each fractionated solution were determined, and the recovery of each of BON6 and BON3 in each fraction and the ratio of BON6 were calculated. The results were shown in FIG. 5.

Each fraction (0.3–2.8) in which BON6 was eluted contains BON3 in the amount of not less than 76% together with BON 6, so that BON6 could not be separated.

Comparative Example 2

The methanol development was carried out according to the same manner to Example 2 except that a cationic ion exchange resin (DIAION SK204H, available from Mitsubishi Kagaku K. K.) was used as an adsorbent.

Figure 6:
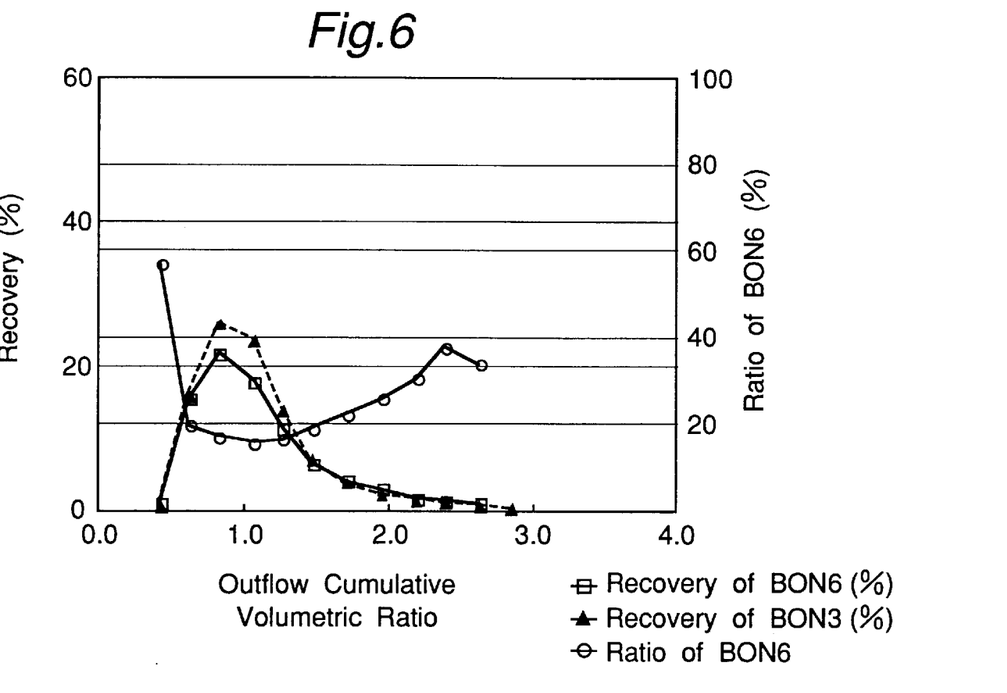
FIG. 6 is a graph illustrating the recovering ratios of each of BON6 and BON3 to the outflow cumulative volumetric ratio, and the change of ratio of BON6 in Comparative Example 2.

According to the same manner as Example 2, each fraction was weighed, the concentrations of BON6 and BON3 in each fractionated solution were determined, and the recoveries of each of BON6 and BON3 in each fraction and the ratio of BON6 were calculated. The results were shown in FIG. 6.

Each fraction (0.4–2.6) in which BON6 was eluted contains BON3 in the amount of not less than 66% together with BON 6, which means that BON6 could not be separated.

Comparative Example 3

The methanol development was carried out according to the same manner as Example 2 except that polyamides (Polyamide C-100, available from Wako Junyaku K. K.) was used as an adsorbent.

Figure 7:
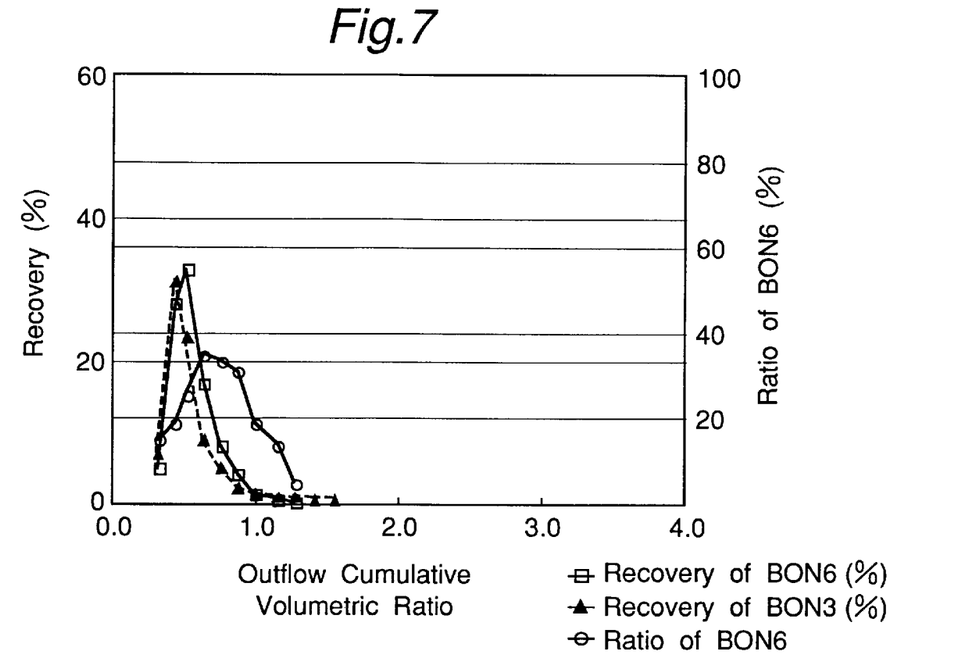
FIG. 7 is a graph illustrating the recovering ratios of each of BON6 and BON3 to the outflow cumulative volumetric ratio, and the change of ratio of BON6 in Comparative Example 3.

According to the same manner as the Example 2, each fraction was weighed, the concentrations of BON6 and BON3 in each fractionated solution were determined, and the recovery of each of BON6 and BON3 in each fraction and the ratio of BON6 were calculated. The results were shown in FIG. 7.

Each fraction (0.4–1.4) in which BON6 was eluted contains BON3 in the amount of not less than 65% together with BON 6, so that BON6 could not be separated.

Comparative Examples 4, 5 and 6

The methanol developments were carried out according to the same manner as Example 2 except that an anionic ion exchange resin (DIAION WA10: available from Mitsubishi Kagaku K. K.), an anionic ion exchange resin (DIAION WA20: available from Mitsubishi Kagaku K. K.), and activated carbon for chromatography (available from Wako Junyaku K. K.) were used as adsorbents respectively.

According to the same manner as the Example 2, each fraction was weighed, the concentrations of BON6 and BON3 in each fractionated solution were determined, but BON6 and BON3 were not detected in any fractions, which were retained in the adsorbents respectively.

Comparative Example 7

The methanol development was carried out according to the same manner as Example 2 except that a silica gel (Wakogel C-200: available from Wako Junyaku K. K.) was used as an adsorbent.

According to the same manner as the Example 2, each fraction was weighed, the concentrations of BON6 and BON3 in each fractionated solution were determined, but BON6 and BON3 were detected in every fraction as they were before this treatment, which flowed out without adsorption.

Example 5

The methanol development was carried out according to the same manner as Example 1 except that the methanol solution 100 g were prepared by dissolving BON6 (18.3 g) and BON3 (2.0 g) in methanol.

Figure 8:
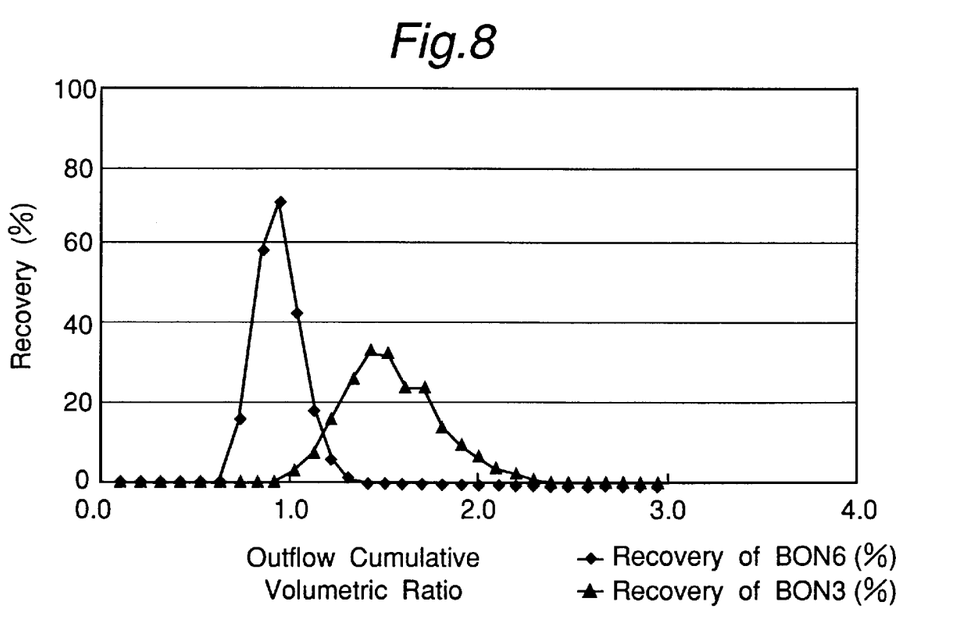
FIG. 8 is a graph illustrating the change of recovering ratios of each of BON6 and BON3 to the outflow cumulative volumetric ratio in Example 5.
Figure 9:
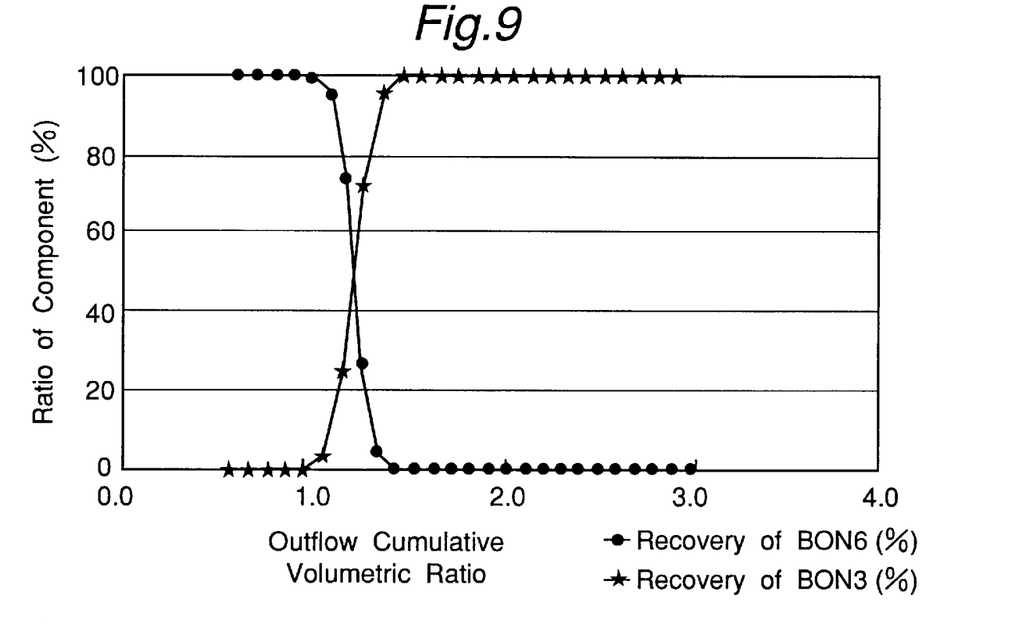
FIG. 9 is a graph illustrating the change of ratio of BON6 to the outflow cumulative volumetric ratio and that of BON3 respectively in Example 5.

According to the same manner as the Example 1, each fraction was weighed, the concentrations of BON6 and BON3 in each fraction were determined, and the recoveries of each of BON6 and BON3 in each fraction (FIG. 8) and the ratios thereof (FIG. 9) were calculated respectively.

BON 6 were recovered in the ratio of not less than 99% and the recovery of 91.7%, and BON3 was recovered in the ratio of not less than 99% and the recovery of 60.0%.

Example 6

The methanol development was carried out according to the same manner as Example 2 except that the methanol solution 100 g were prepared by dissolving BON6 (18.3 g) and BON3 (2.0 g) in methanol.

Figure 10:
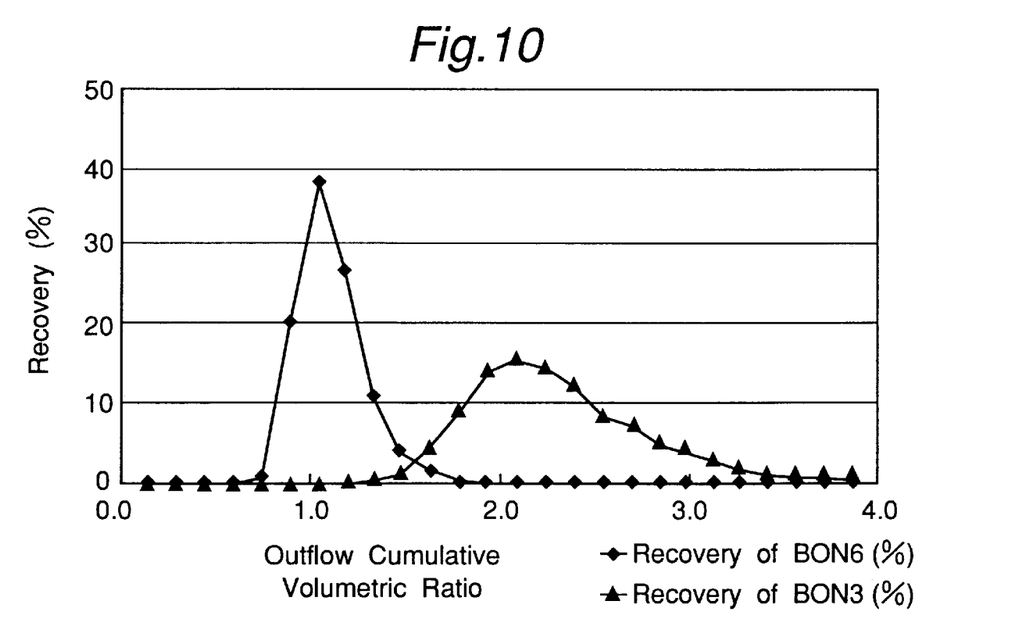
FIG. 10 is a graph illustrating the change of recovering ratios of each of BON6 and BON3 to the outflow cumulative volumetric ratio in Example 6.
Figure 11:
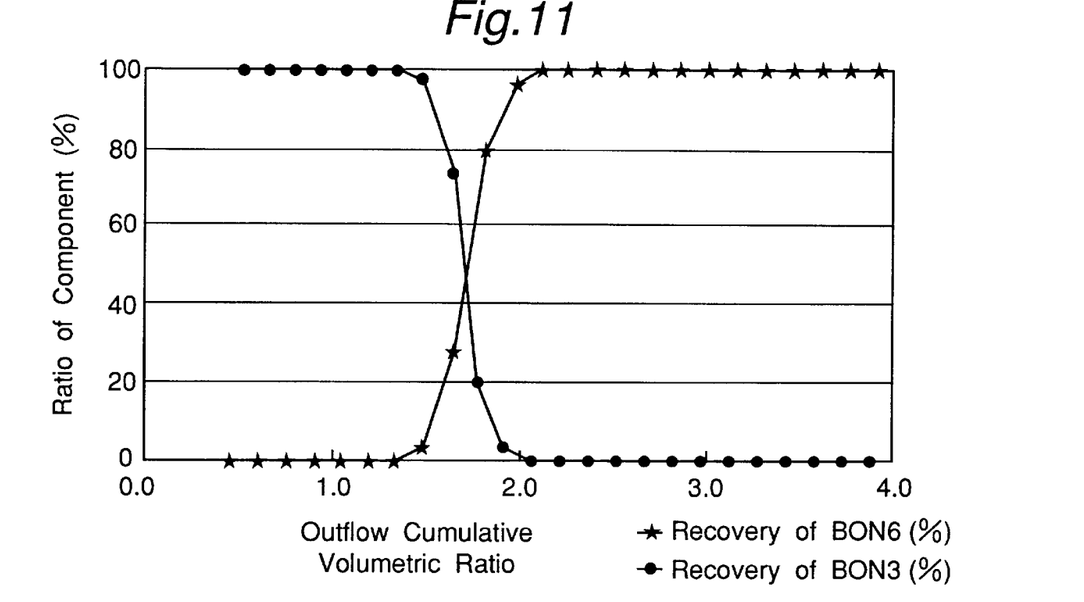
FIG. 11 is a graph illustrating the change of ratio of BON6 to the outflow cumulative volumetric ratio and that of BON3 respectively in Example 6.

According to the same manner as the Example 2, each fraction was weighed, the concentrations of BON6 and BON3 in each fraction were determined, and the recoveries of each of BON6 and BON3 in each fraction (FIG. 10) and the ratios thereof (FIG. 11) were calculated respectively.

BON 6 was recovered in the ratio of not less than 99% and the recovery of 96.4%, and BON3 was recovered in the ratio of not less than 99% and the recovery of 71.0%.

Example 7

The methanol development was carried out according to the same manner as Example 2 except that the methanol solution 100 g were prepared by dissolving BON6 (0.25 g), BON3 (0.24 g) and BON3,6 (0.72 g) in methanol.

Figure 12:
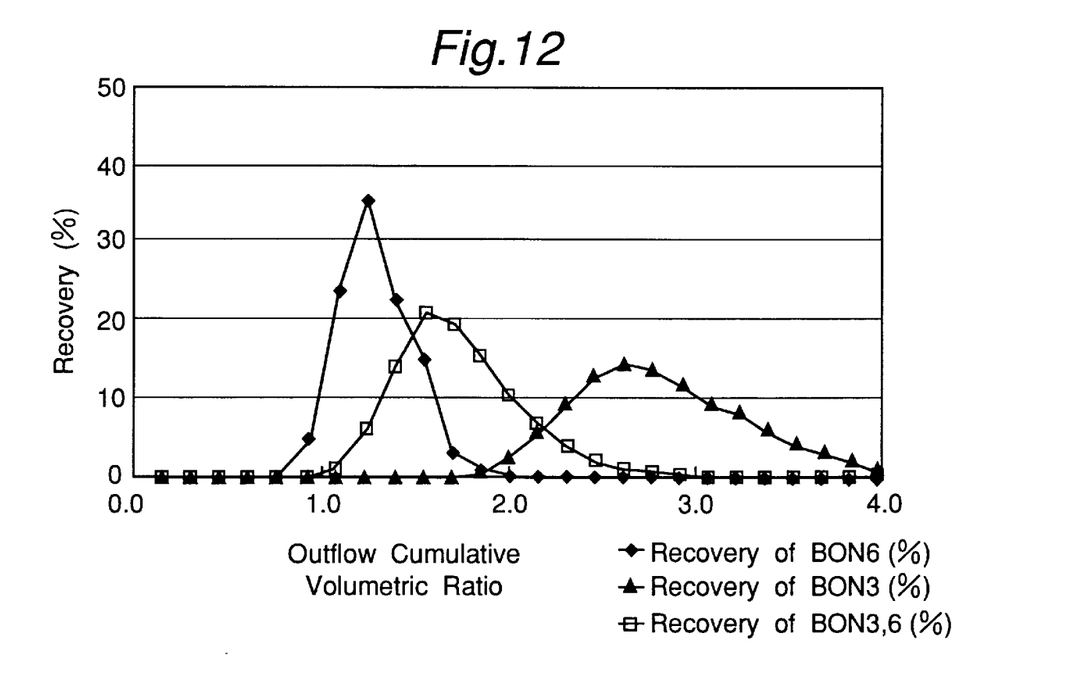
FIG. 12 is a graph illustrating the change of recovering ratios of each of BON6, BON3 and BON3,6 to the outflow cumulative volumetric ratio in Example 7.
Figure 13:
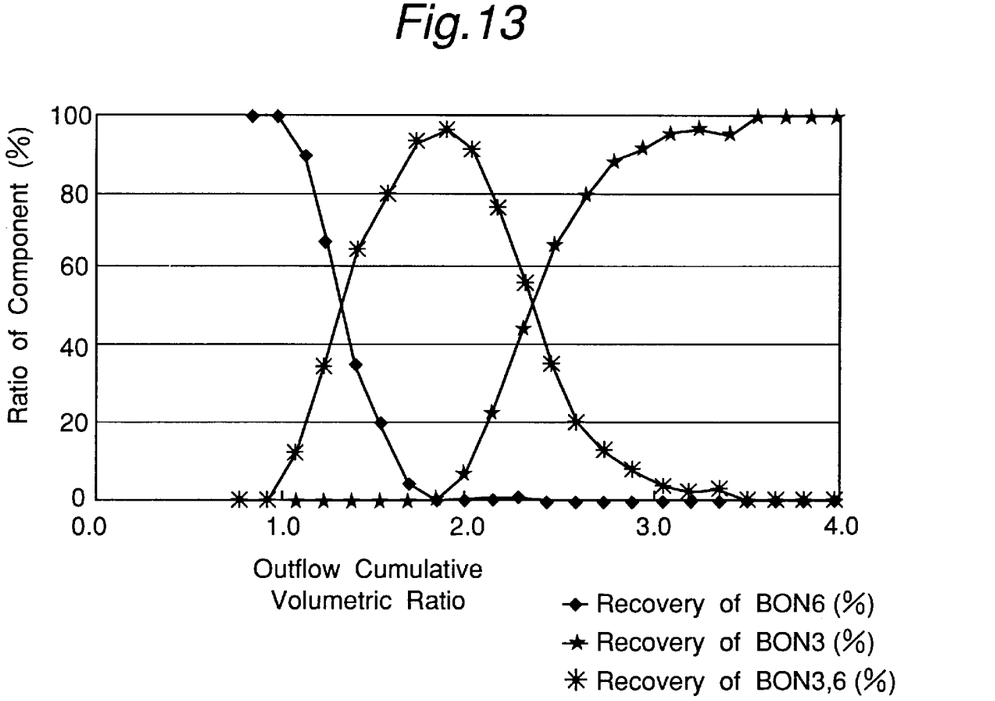
FIG. 13 is a graph illustrating the change of ratio of BON6 to the outflow cumulative volumetric ratio and those of BON3 and BON3,6 respectively in Example 7.

According to the same manner as the Example 2, each fraction was weighed, the concentrations of BON6, BON3 and BON3,6 in each fraction were determined, and the recoveries of each of BON6, BON3 and BON3,6 in each fraction (FIG. 12) and the ratios thereof (FIG. 13) were calculated respectively.

BON 6 was recovered in the ratio of not less than 66% and the recovery of 62.1%, BON3 was recovered in the ratio of not less than 91% and the recovery of 44.0%, BON3,6 was recovered in the ratio of not less than 93% and the recovery of 64.8%.

Comparative Example 8

The methanol development was carried out according to the same manner as Example 7 except that activated carbons for chromatography (available from Wako Junyaku K. K.) was used as an adsorbent.

According to the same manner as the Example 7, each fraction was weighed, the concentrations of BON6, BON3 and BON3,6 in each fractionated solution were determined, but BON6, BON3 and BON3,6 were not detected in any fraction, which were retained as adsorbed.

Comparative Example 9

The methanol development was carried out according to the same manner as Example 7 except that a silica gel (Wakogel C-200: available from Wako Junyaku K. K.) was used as an adsorbent.

According to the same manner as the Example 7, each fraction was weighed, the concentrations of BON6, BON3 and BON3,6 in each fractionated solution were determined, but BON6, BON3 and BON3,6 were detected as they were in every fraction, which were not adsorbed and flowed out.

As an above result, hydroxynaphthalene-carboxylic acids such as BON3, BON6, BON3,6 and the like can be separated and purified using a nonionic porous synthetic adsorbent having as a basic structure aromatic copolymers mainly composed of styrene and divinylbenzene or methacryl copolymers mainly composed of monomethacrylates and dimethacrylates.

What we claim are:

1. A method of separation and purification of hydroxynaphthalenecarboxylic acids which comprises treating a solution containing a mixture of two or more kinds of hydroxynaphthalenecarboxylic acids with a nonionic porous synthetic adsorbent having as a basic structure aromatic copolymers mainly composed of styrene and divinylbenzene as main monomers or methacryl copolymers mainly composed of monomethacrylates and dimethacrylates.

2. A method of separation and purification of claim 1, in which the mixture of hydroxynaphthalene-carboxylic acids contains at least two kinds of compounds selected from 2-hydroxynaphthalene-3-carboxylic acid, 2-hydroxynaphthalene-6-carboxylic acid and 2-hydroxynaphthalene-3,6-dicarboxylic acid.

3. A method of separation and purification of claim 1, in which the treatment with an adsorbent is carried out by adsorption column chromatography.

* * * * *